United States Patent [19]
Lusson

[11] Patent Number: 5,874,659
[45] Date of Patent: Feb. 23, 1999

[54] PROCESS FOR THE PREPARATION OF P-BROMOTOLUENE

[75] Inventor: Christophe-Henri Pierre Lusson, Chateau-Annoux, France

[73] Assignee: Albemarle Corporation, Richmond, Va.

[21] Appl. No.: 78,380

[22] Filed: May 13, 1998

[51] Int. Cl.⁶ .................................................. C07C 22/00
[52] U.S. Cl. .......................................... 570/211; 570/206
[58] Field of Search ...................................... 570/211, 206

[56] References Cited

U.S. PATENT DOCUMENTS

| | | | |
|---|---|---|---|
| 4,571,441 | 2/1986 | Miwa et al. | 570/211 |
| 4,605,799 | 8/1986 | Miwa | 570/211 |
| 4,794,202 | 12/1988 | Zinnen | 570/211 |
| 4,962,245 | 10/1990 | Kanai et al. | 570/211 |
| 5,152,875 | 10/1992 | Rittner et al. | 570/211 |

FOREIGN PATENT DOCUMENTS

| | | |
|---|---|---|
| 1091731 | 9/1994 | China . |
| 247989 | 12/1987 | Czech Rep. . |
| 1066032 | 4/1967 | United Kingdom . |

OTHER PUBLICATIONS

Abstract–Derwent–of JP 04308542, Oct. 1992.
Chmical Engineers' Handbook, 5th Edition, McGraw–Hill Book Company, 1973, pp. 17–19 through 17–26.

*Primary Examiner*—Alan Siegel
*Attorney, Agent, or Firm*—E. E. Spielman, Jr.

[57] ABSTRACT

A crude bromotoluene mixture comprising at least 70 wt % of a mixture of p-bromotoluene and o-bromotoluene, and wherein the weight ratio of p-bromotoluene:o-bromotoluene is in the range of 50:50 to 99:1 is cooled to a temperature at which crystals of product enriched in p-bromotoluene are formed in a first residual mother liquor. After removing the residual mother liquor from the crystals of product enriched in p-bromotoluene, the crystals are partially melted to form a mixture of residual higher purity p-bromotoluene in the form of crystals, and a second mother liquor having a higher content of o-bromotoluene than said first residual mother liquor. This higher purity p-bromotoluene and the second mother liquor are separated from each other. The entire procedure starting with the above cooling step can be repeated as a second stage and again as a third stage each time using as the initial feed the residual higher purity p-bromotoluene that is separated from the second mother liquor of the preceding stage. Product of 99.5 wt % purity can be formed in this manner.

27 Claims, 4 Drawing Sheets

PROCESS FOR THE PREPARATION OF P-BROMOTOLUENE

BACKGROUND

Over the years various attempts have been made to devise effective process technology for producing p-bromotoluene in good yield and of high purity. This has proven to be a difficult task, as most processes tend to produce mixtures of o-bromotoluene along with p-bromotoluene. Because of their close boiling points the separation of these isomers from each other in a large scale plant installation requires a distillation column of very high efficiency.

The magnitude of the problem and the extensive efforts that have been devoted toward producing either o-bromotoluene or p-bromotoluene in high yield and purity is illustrated by the following sampling of published accounts of research in the field:

U.S. Pat. No. 3,303,224 (1967) describes use of $BaBrO_3$ with one equivalent of $H_2SO_4$ and oxalic acid to brominate toluene in an aqueous medium, followed by extraction with methylene chloride. An 85% yield of a bromotoluene fraction was obtained. Infrared analysis indicated the product to be 66% ortho-, 33% p- and 1% m-bromotoluene.

Japan Kokai 52-042825 (1977) describes refluxing a 51:49 para-ortho) mixture of bromotoluenes with beta-cyclodextrin in 75% aqueous acetic acid followed by extracting the precipitate with hot diethyl ether to obtain 99.5-0.5 ortho-para. The liquid phase from which the precipitate had been removed gave a mixture of 28% o-bromotoluene and 72% p-bromotoluene.

Japan Kokai 57-077631 (1982) refers, inter alia, to vapor phase bromination of toluene using as catalysts, zeolites with average pore diameters of 5 to 13 Angstroms.

*Organometallics*, 1986, 5(1), 168–173 refers, inter alia, to bromination of tolyl(octaethylporphinato)rhodium to produce bromotoluene with high regioselectivity.

*J. Chem. Soc., Chem. Commun.*, 1987, 10, 752–3; *J Org. Chem.*, 1988, 53(23), 5545–7; and Israel 79627 A1 (1992) refer, inter alia, to formation of p-bromotoluene by use of BrF as the brominating agent.

*J. Org. Chem.* 1988, 53(9), 2093–4 refers to use of $CuBr_2$ adsorbed onto alumina as a selective brominating agent. Synthesis of p-bromotoluene is referred to.

*Zeolites*, 1987,7(6), 499–502 describes ring bromination of alkylbenzenes, including toluene, using zeolite 13X or mordenite after introduction of Fe (III) ions.

*J. Chem. Soc., Chem. Commun.*, 1989, 10, 653–4 indicates that propylene oxide, acting as an HBr scavenger, greatly improved the selectivity of zeolite-catalyzed bromination of toluene to form almost pure p-bromotoluene.

*Zeolites*, 1991, 11(6), 617–21 describes results from a study of the liquid phase bromination of aromatics, including toluene, catalyzed by zeolites. An explanation is given for the low selectivities obtained even though zeolite catalysts are used.

*Synth. Commun.*, 1992, 22(8), 1095–9 describes formation of 65:35 mixtures of ring-brominated derivatives of toluene using molecular bromine adsorbed on the surface of alumina, and no solvent. A 90% yield was achieved.

*Synth. Commun.*, 1992, 22(17), 2513–20 refers to preparation of p-bromotoluene from bromination of toluene with bromosaccharin in pyridinium poly(hydrogen fluoride).

*J. Chem. Soc. Pak.*, 1992, 14(3), 212–14 reports formation of p-bromotoluene in 70% yield by use of a mixture of KBr and $NaNO_3$ in sulfuric acid (60% vol./vol.).

*Ind. Chem. Libr.*, 1995, 7, 17–28 refers to use of cupric bromide supported on alumina to brominate, inter alia, toluene.

*Ind. Chem. Libr.*, 1995, 7, 49–64 indicates that toluene can be brominated in quantitative yield and with excellent para-selectivity by use of tert-butyl hypobromite in the presence of proton-exchanged zeolite X.

*Chem. Commun. (Cambridge)*, 1996, 4, 467–8 indicates that toluene can be brominated with bromine and a stoichiometric amount of zeolite NaY in high yield and with high selectivity to p-bromotoluene, and that the zeolite is easily regenerated by heating.

p-Bromotoluene is an important intermediate for the commercial synthesis of bioactive compounds by at least two large industrial concerns. Although some of the foregoing methods are effective for producing p-bromotoluene in high yields and good selectivities in laboratory-scale operations, the need exists for an efficient process which can provide high purity p-bromotoluene in good yields on an industrial scale and within the limits of economic constraints. It is believed that this invention makes possible the achievement of these objectives.

SUMMARY OF THE INVENTION

This invention provides in one of its embodiments a process for the preparation of p-bromotoluene which comprises:

a) providing a crude bromotoluene mixture comprising at least 85 wt % of a mixture of p-bromotoluene and o-bromotoluene, and wherein said mixture contains at least 55 wt % p-bromotoluene and at least 30 wt % o-bromotoluene, said crude mixture being formed by a process comprising liquid phase bromination of toluene;

b) cooling said crude bromotoluene mixture to a temperature at which crystals of product enriched in p-bromotoluene are formed in a first residual mother liquor;

c) removing at least a portion of said first residual mother liquor from the crystals of product enriched in p-bromotoluene;

e) partially melting said crystals to produce a mixture of higher purity p-bromotoluene in the form of crystals, and a second mother liquor having a higher content of o-bromotoluene than said first residual mother liquor; and f) separating said higher purity p-bromotoluene and said second mother liquor from each other. Economic evaluations have indicated that the above process is more attractive than the conventional industrial process involving production from p-toluidine using the Sandmeyer reaction.

FURTHER DETAILED DESCRIPTION

Figure 1:
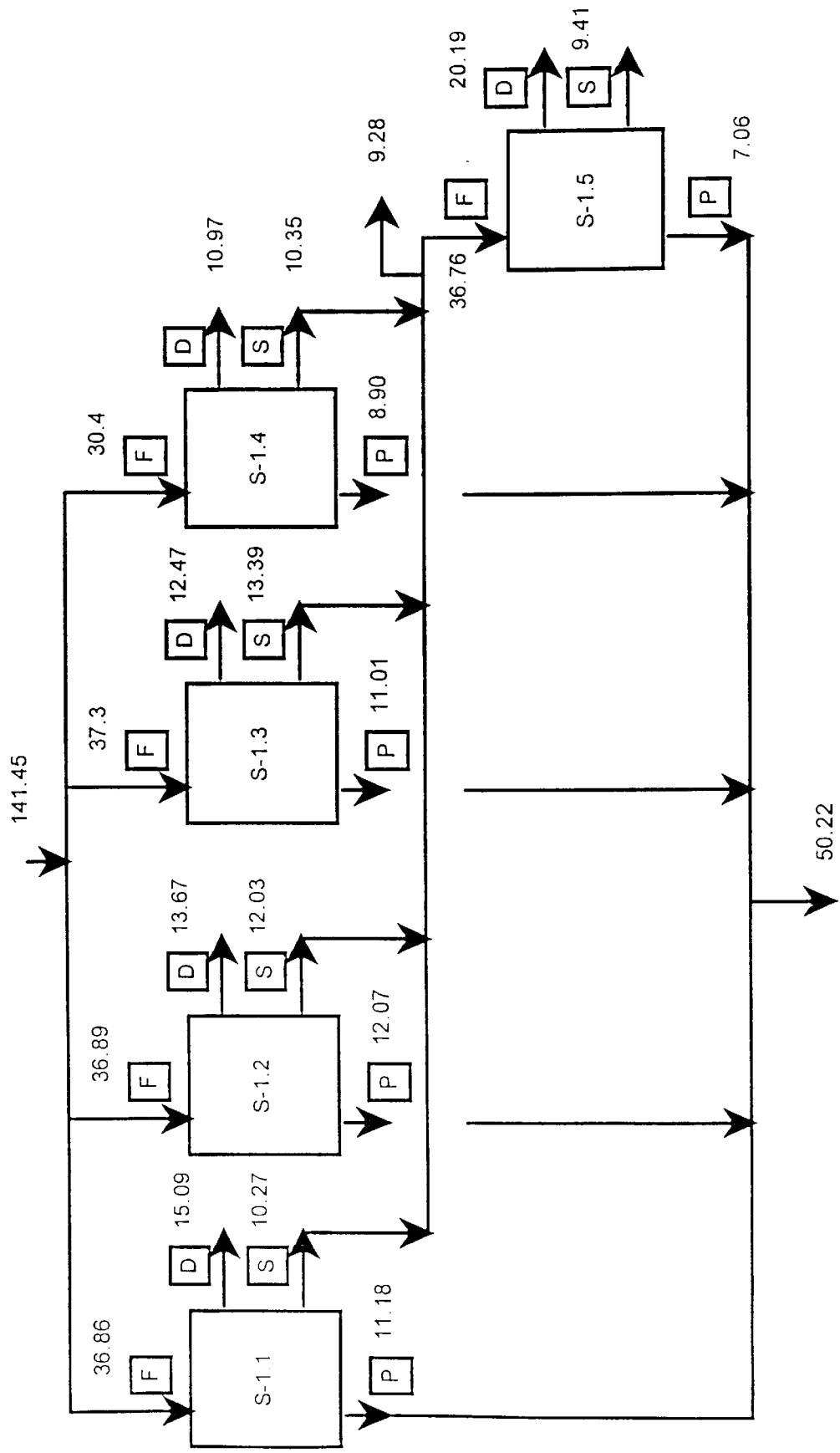
FIG. 1 is a schematic flow diagram of a pilot plant operation conducted to simulate first stage operation of a process of this invention.

The liquid phase bromination of toluene with bromine can be conducted either in bulk or in a suitable liquid organic solvent that is substantially inert to the reactants and the products of the reaction. In either case it is preferable to employ the reactants in proportions of 0.8 to 1.2 moles of toluene per mole of bromine ($Br_2$). Reaction temperatures are typically in the range of −15° to 200° C. and preferably in the range of 15° to 70° C. Suitable ancillary solvents that can be used include individual or mixtures of saturated halohydrocarbons, such as methylene dibromide, methylene dichloride, ethylene dibromide, ethylene dichloride, chloroform, carbon tetrachloride, 1,1,1-trichlorethane, 1,1,2-trichloroethane, etc., individual or mixtures of saturated hydrocarbons such as straight or branched chain pentanes, hexanes, heptanes, octanes, nonanes, decanes, cyclohexane, methylcyclohexane, one or more dimethylcyclohexanes, etc., individual or mixtures of saturated monoethers or polyethers such as diethyl ether, dibutyl ether, methyl-tert-butyl ether, ethyl-tert-butyl ether, methyl-tert-amyl ether, tetrahydrofuran, methyltetrahydrofuran, tetrahydropyran, 1,2-dimethoxyethane, 1,2-diethoxyethane, diglyme, triglyme, 1,3-dioxolane, 1,4-dioxane, 2-methyl-1,3-dioxolane, etc., individual or mixtures of liquid perfluorocarbons or perfluorohalocarbons including perfluorohexanes, perfluoroheptanes, perfluorooctanes, perfluorohexylbromide, etc., mixtures of different types of such solvents. Other suitable, equivalent types of solvents will now be apparent to those skilled in the art. Preferably the bromine is fed continuously and/or incrementally into the toluene. While the process can be conducted in the absence of a catalyst, it is preferred to use a catalytic quantity of a Lewis acid such as $AlCl_3$, $ZnCl_2$, or $FeCl_3$. Care should be taken to avoid use of an excessive amount of catalyst as this can lead to over-bromination. Thus typically the amount of Lewis acid catalyst will fall in the range of 0.00005 to 1 mole of Lewis acid per mole of bromine used. Preferably the amount of Lewis acid catalyst used will fall in the range of 0.005 to 0.15 mole of Lewis acid per mole of bromine being used.

A mixture composed predominately of p-bromotoluene and o-bromotoluene, plus ancillary solvent if used, is produced by the bromination reaction. When a solvent is present, it is separated from the brominated toluene products by solvent distillation, solvent extraction, chromatographic, or like procedures. Preferably a solvent is used that can be distilled or flashed away at one or more temperatures well below the boiling temperature of the p-bromotoluene (ca. 184° C. at 760 mm Hg). The initial product mixture utilized in the ensuing crystallization separations should comprise at least 70 wt %, and preferably at least 85 wt %, of a mixture of p-bromotoluene and o-bromotoluene in which the p-bromotoluene:o-bromotoluene ratio is in the range of 50:50 to 99:1, and preferably in the range of 55:45 to 90:10.

In the initial crystallization step the temperature of the foregoing initial product mixture is reduced, typically from ambient room temperature (although the temperature could be higher), to a temperature in the range of −25° to 35° C. such that the product is converted at least partially into crystals of product depleted of some o-bromotoluene (and thus enriched in p-bromotoluene) with the remainder as a first liquid phase enriched in o-bromotoluene. The system is then held at this same temperature for a period of 0.1 to 10 hours, and during this time the liquid phase is drawn off from the crystals as "drained material" (also often referred to as "dripped materials" or "drippings"). At the end of this holding period the temperature of the crystals is raised to a temperature in the range of −25° to 35° C. to partially melt the crystals to thereby provide residual crystals further enriched in p-bromotoluene, and the system is held at this temperature for 0.1 to 10 hours. During this second holding period the liquid phase is drained off from the residual crystals as "partially melted material" or "sweated material". The crystals are then melted and either recovered as a purified product, or this entire procedure is repeated one or more times (as the second stage, and then the third stage, etc.) each time using the final melted product enriched in p-bromotoluene as the feed to the next stage.

The liquid phase from the freezing step and/or from the fractional melting step can be recycled as a portion of the feed to an ensuing separation/purification operation conducted in the same general fashion.

Apparatus suitable for conducting these freezing and fractional melting operations is described, for example, in Zief and Wilcox, *Fractional Solidification*, Volume I, for example at page 393.

By the practice of this invention an initial bromination product containing 60.9% p-bromotoluene and 33% o-bromotoluene, formed as described herein, was subjected to the above freezing and fractional melting procedures. It was found that a purified p-bromotoluene product of 98% purity was obtained. The calculated yield was 60%, and with concentration of the liquid phases, a yield of 80% was achievable on the basis of the estimated composition of the eutectic composition.

Depending upon the final purity of the p-bromotoluene desired, at least two purification stages should be used in order to achieve a purity of 98% of the para-isomer. For a purity of at least about 99.5%, a three-stage operation should be used.

Each stage involves the following operations: (a) Feeding the apparatus and precooling the product charge, (b) crystallizing the product charge, (c) causing the liquid mother liquor to separate from the frozen product by dripping (a gravity-induced separation yielding the drained material), (d) partially melting or "sweating" the crystals in order to form a liquid film surrounding the crystals, which film contains more of the impurities than the residual unmelted crystals, (e) removing the partially melted or sweated material, and (f) melting the residual higher purity crystals remaining in the apparatus and thereby evacuating the apparatus with a flow of purified product to be used as the product charge to the next stage where a next stage is used.

In a full scale industrial plant using the process of this invention the drained or dripped material is recycled to the preceding stage (where there is a preceding stage), or to the same stage (a) in the case of the first stage of a multi-stage operation or (b) in the case of a single stage operation. The sweated material is typically recirculated as feed to the same unit (i.e., to the same stage) from which it was derived.

Figure 2:
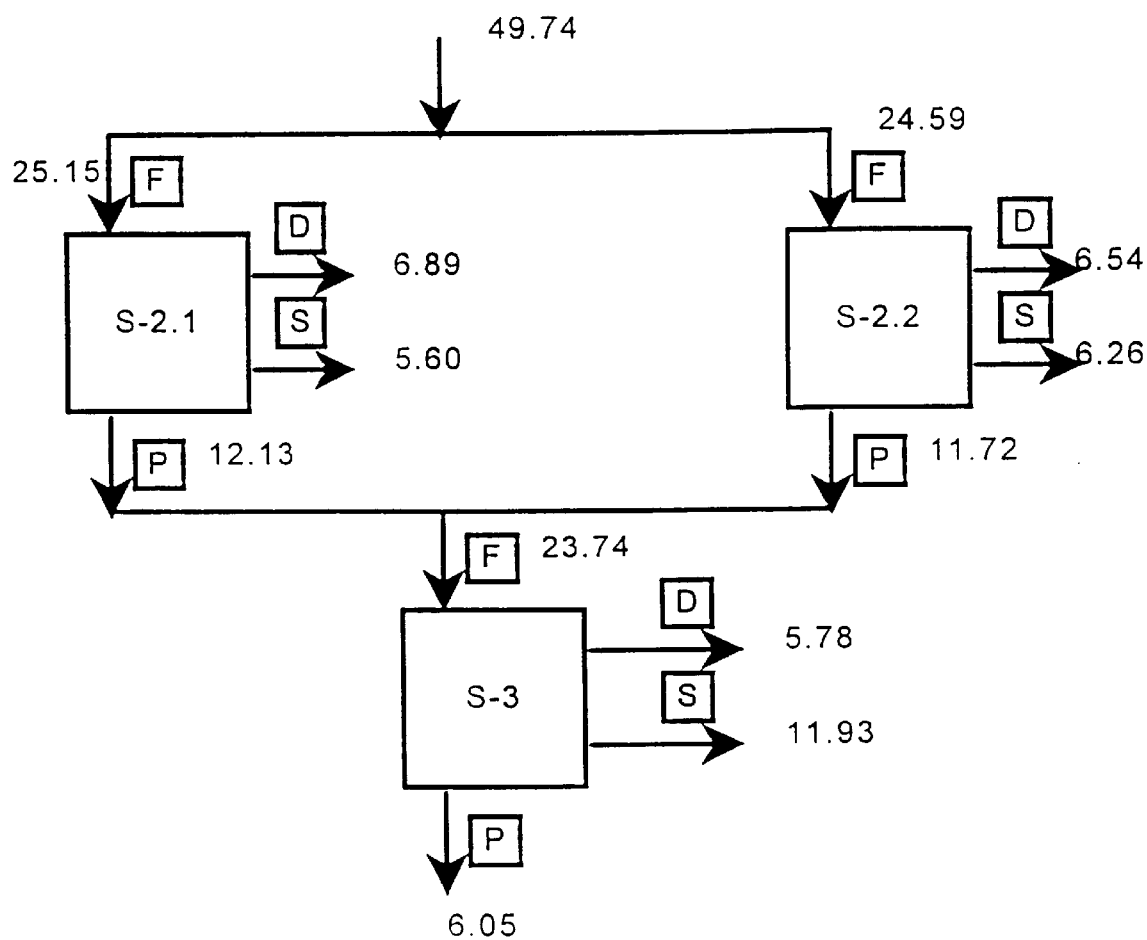
FIG. 2 is a schematic flow diagram of a pilot plant operation conducted to simulate second stage and third stage operations of a process of this invention.

In order to properly simulate operation in a large scale commercial installation, a pilot plant operation was conducted wherein four first stage operations were first conducted and the cooling fractions from these four stages were used to actualize a "fifth first stage". FIG. 1 schematically illustrates the flows involved in the foregoing operations. The numerals for the flows represent amounts in kilograms. The total amount of product recovered at the end of these stages was used to conduct two second stages, without recycling. The amount obtained at the end of these two second stages was used to conduct the third and last purification stage. FIG. 2 illustrates the flows involved in these second and third stage operations. Again the numerals given by the flows represents amounts or mass in kilograms. In FIGS. 1 and 2, the feed streams are labelled "F", the flows of drained or dripped material are labelled "D", the flows of partially melted or sweated material are labelled "S", and the flows of purified material are labelled "P".

The Table sets forth the partition coefficient obtained during the different stages of the pilot plant of operation, the partition coefficient being defined as the total mass withdrawn during the particular fed-in mass stage.

TABLE

Partition Coefficients

| Stage | Drained or Dripped Material | Partially Melted or Sweated Material |
|---|---|---|
| S-1.1 | 0.409 | 0.278 |
| S-1.2 | 0.371 | 0.326 |
| S-1.3 | 0.334 | 0.359 |
| S-1.4 | 0.368 | 0.341 |
| Average S-1 | 0.371 | 0.326 |
| S-2.1 | 0.274 | 0.223 |
| S-2.2 | 0.266 | 0.255 |
| Average S-2 | 0.270 | 0.239 |
| S-3 | 0.244 | 0.503 |

Figure 3:
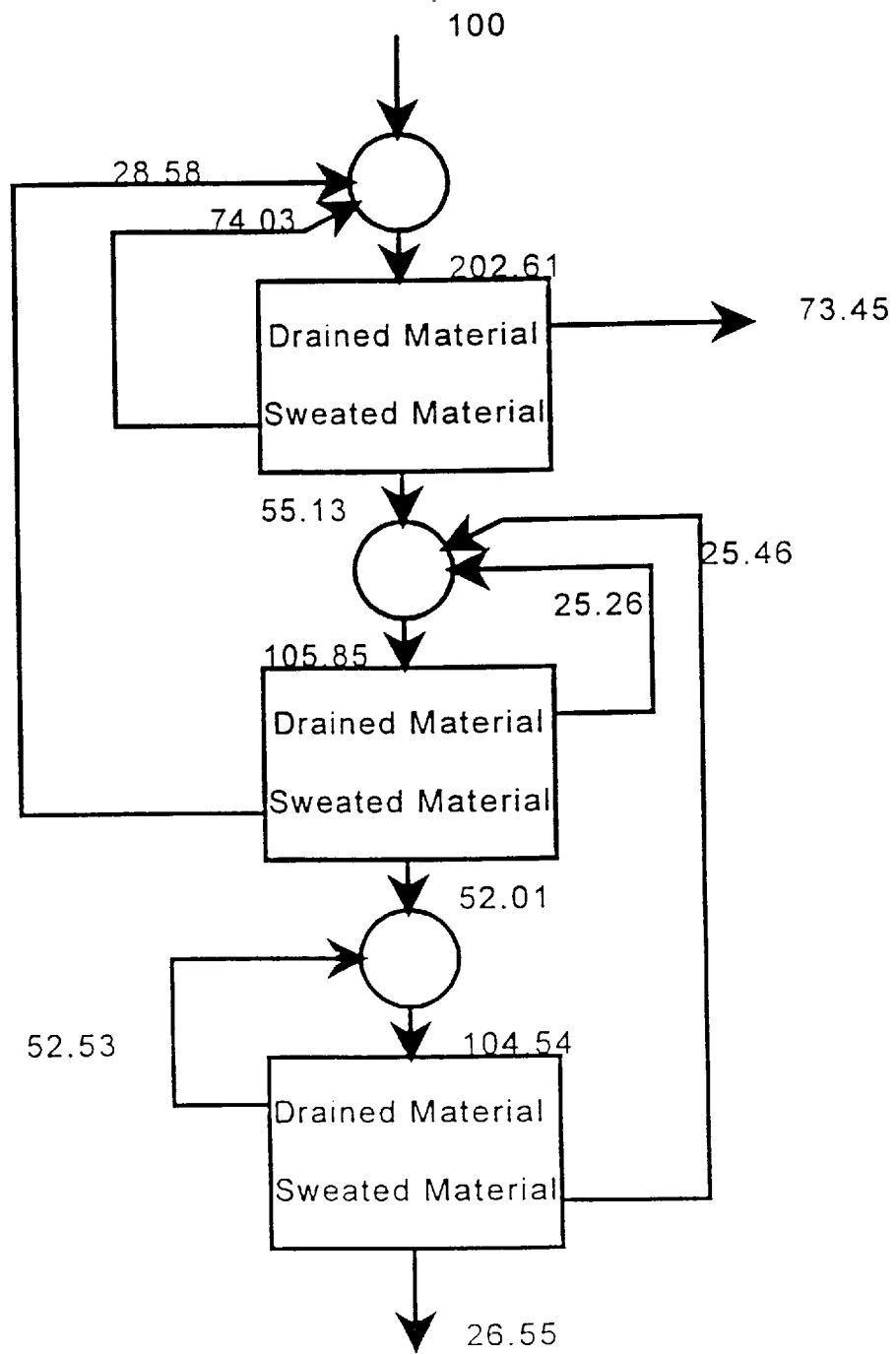
FIG. 3 is a schematic flow diagram of a three-stage plant operation with recycle, and showing mass balances derived from the pilot plant operations of FIGS. 1 and 2, wherein the numerals for the flows are in terms of kilograms.
Figure 4:
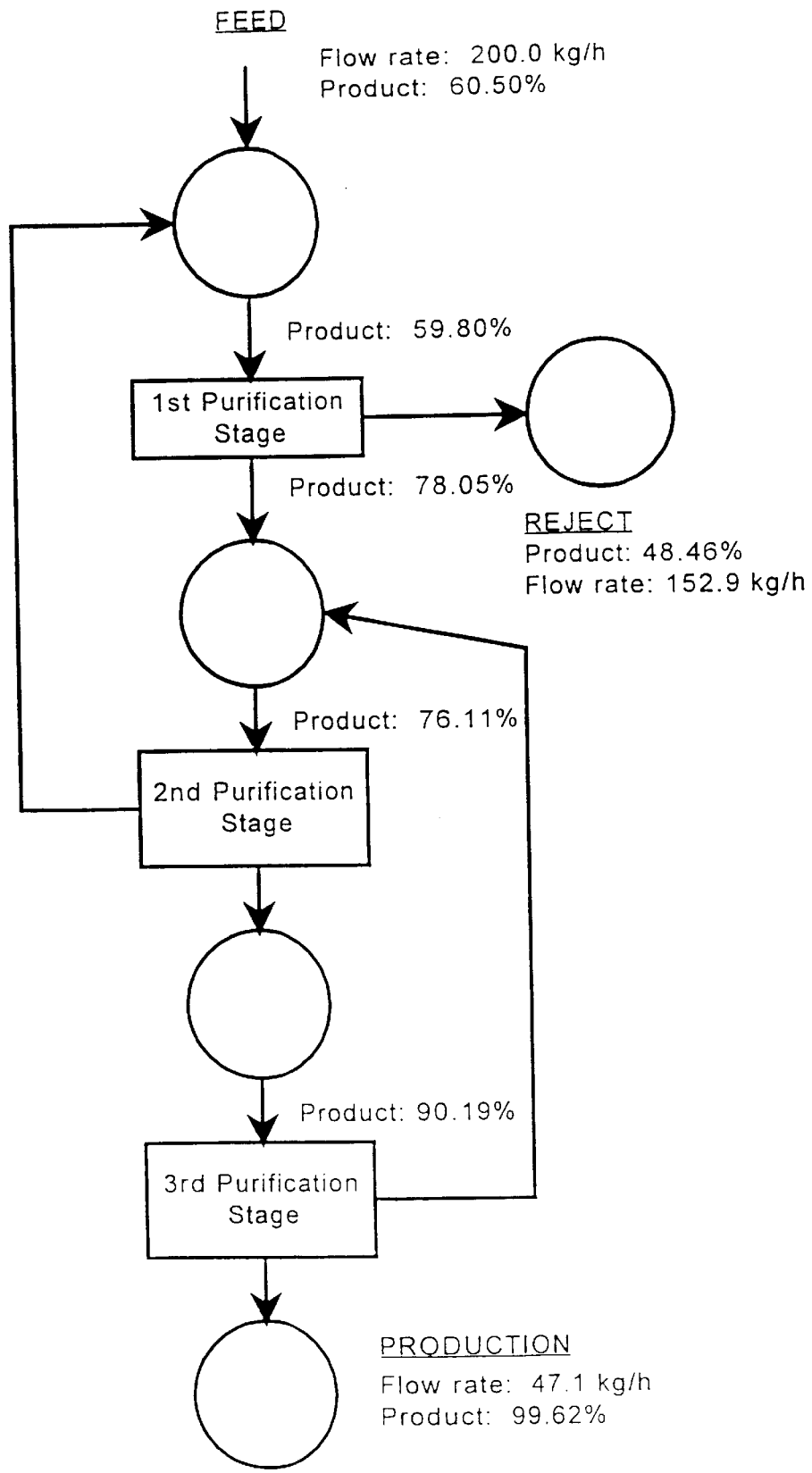
FIG. 4 is a schematic flow diagram of a three-stage plant operation with recycle, and showing overall mass balance and flow rates based on the results obtained in the pilot plant operation for obtaining a product with a purity of 99.5% p-bromotoluene, wherein the numerals for the flows are in terms of kilograms.

The efficacy of the process of this invention is illustrated schematically by the flows and mass balances as set forth in FIGS. 3 and 4 based on the pilot plant operations and partition coefficients described above.

I claim:

1. A process for the preparation of p-bromotoluene which comprises:
    a) providing a crude bromotoluene mixture comprising at least 70 wt % of a mixture of p-bromotoluene and o-bromotoluene wherein the weight ratio of p-bromotoluene:o-bromotoluene is in the range of 50:50 to 99:1;
    b) cooling said crude bromotoluene mixture to a temperature at which crystals of product enriched in p-bromotoluene are formed in a first residual mother liquor;
    c) removing at least a portion of said first residual mother liquor from the crystals of product enriched in p-bromotoluene;
    d) partially melting said crystals to produce a mixture of residual higher purity p-bromotoluene in the form of crystals, and a second mother liquor having a higher content of o-bromotoluene than said first residual mother liquor; and
    e) separating said second mother liquor and said higher purity p-bromotoluene from each other.

2. A process according to claim 1 wherein said crude mixture is formed by a process comprising liquid phase bromination of toluene.

3. A process according to claim 2 wherein said liquid phase bromination of toluene is conducted in bulk.

4. A process according to claim 2 wherein the liquid phase bromination of toluene is conducted in a liquid inert ancillary solvent.

5. A process according to claim 1 wherein at least said first residual mother liquor is recycled from c) to b).

6. A process according to claim 1 wherein at least said second mother liquor is recycled to from e) to b) or d).

7. A process according to claim 1 wherein said first residual mother liquor is recycled from c) to b) and said second mother liquor is recycled from e) to b) or d).

8. A process according to claim 1 wherein the higher purity p-bromotoluene is subjected to steps b), c), d), and e) in a second stage to produce a still higher purity p-bromotoluene.

9. A process according to claim 8 wherein the still higher purity p-bromotoluene has a purity of at least 98.0 weight percent.

10. A process according to claim 8 wherein the recovered still higher purity p-bromotoluene from the second stage is subjected to steps b), c), d), and e) in a third stage to produce an even higher purity p-bromotoluene.

11. A process according to claim 10 wherein the even higher purity p-bromotoluene has a purity of at least 99.5 weight percent.

12. A process according to claim 1 wherein at least said first residual mother liquor is recycled from c) to b), and wherein the higher purity p-bromotoluene is subjected to steps b), c), d), and e) in a second stage to produce a still higher purity p-bromotoluene.

13. A process according to claim 12 wherein the still higher purity p-bromotoluene has a purity of at least 98.0 weight percent.

14. A process according to claim 12 wherein the recovered still higher purity p-bromotoluene from the second stage is subjected to steps b), c), d), and e) in a third stage to produce an even higher purity p-bromotoluene.

15. A process according to claim 14 wherein the even higher purity p-bromotoluene has a purity of at least 99.5 weight percent.

16. A process according to claim 1 wherein at least said second mother liquor is recycled to from e) to b) or d), and wherein the higher purity p-bromotoluene is subjected to steps b), c), d), and e) in a second stage to produce a still higher purity p-bromotoluene.

17. A process according to claim 16 wherein the still higher purity p-bromotoluene has a purity of at least 98.0 weight percent.

18. A process according to claim 16 wherein the recovered still higher purity p-bromotoluene from the second stage is subjected to steps b), c), d), and e) in a third stage to produce an even higher purity p-bromotoluene.

19. A process according to claim 18 wherein the even higher purity p-bromotoluene has a purity of at least 99.5 weight percent.

20. A process according to claim 1 wherein said first residual mother liquor is recycled from c) to b) and said second mother liquor is recycled from e) to b) or d), and wherein the higher purity p-bromotoluene is subjected to steps b), c), d), and e) in a second stage to produce a still higher purity p-bromotoluene.

21. A process according to claim 20 wherein the still higher purity p-bromotoluene has a purity of at least 98.0 weight percent.

22. A process according to claim 20 wherein the recovered still higher purity p-bromotoluene from the second stage is subjected to steps b), c), d), and e) in a third stage to produce an even higher purity p-bromotoluene.

23. A process according to claim 22 wherein the even higher purity p-bromotoluene has a purity of at least 99.5 weight percent.

24. A process according to claim 20 wherein said crude mixture is formed by a process comprising liquid phase bromination of toluene conducted in bulk.

25. A process according to claim 20 wherein said crude mixture is formed by a process comprising liquid phase bromination of toluene conducted in a liquid inert ancillary solvent.

26. A process according to claim 22 wherein said crude mixture is formed by a process comprising liquid phase bromination of toluene conducted in bulk.

27. A process according to claim 22 wherein said crude mixture is formed by a process comprising liquid phase bromination of toluene conducted in a liquid inert ancillary solvent.

* * * * *